United States Patent [19]

Sieja

[11] Patent Number: 5,133,838
[45] Date of Patent: Jul. 28, 1992

[54] PURIFICATION OF 6-AMINOCAPRONITRILE

[75] Inventor: James B. Sieja, Wilmington, Del.

[73] Assignee: E. I. Du Pont de Nemours and Company, Wilmington, Del.

[21] Appl. No.: 662,209

[22] Filed: Feb. 28, 1991

[51] Int. Cl.$^5$ ................... B01D 3/34; C07C 255/00
[52] U.S. Cl. ...................... 203/29; 203/38; 203/89; 203/91; 558/452
[58] Field of Search ............. 203/29, 32, 38, 6, 89, 203/91; 558/452

[56] References Cited

U.S. PATENT DOCUMENTS

| 2,867,651 | 1/1959 | Wise | 203/32 |
| 2,900,310 | 8/1959 | Ottenheym | 558/452 |
| 3,159,276 | 12/1964 | Moore | 260/404 |
| 3,207,790 | 9/1965 | Glew et al. | 252/397 |
| 4,379,024 | 4/1983 | Gardner | 203/32 |
| 4,433,194 | 2/1984 | Symon et al. | 203/29 |
| 4,461,676 | 7/1984 | DelPesco et al. | 203/29 |

FOREIGN PATENT DOCUMENTS

| 43-4494 | 2/1968 | Japan | 558/452 |
| 47-3096 | 1/1972 | Japan | 558/452 |

Primary Examiner—Wilbur Bascomb, Jr.
Attorney, Agent, or Firm—Earl L. Handley

[57] ABSTRACT

Purification of 6-aminocapronitrile by reduction of tetrahydroazepine with a hydride, and then distilling the 6-aminocapronitrile at a pot temperature of less than about 200° C.

4 Claims, No Drawings

PURIFICATION OF 6-AMINOCAPRONITRILE

FIELD OF THE INVENTION

This invention relates to the preparation of purified 6-aminocapronitrile from a mixture containing tetrahydroazepine by converting the tetrahydroazepine to hexamethyleneimine and N-(5-cyanopentyl-1,6-hexamethylenediamine, and then recovering 6-aminocapronitrile by controlled distillation. The 6-aminocapronitrile is then sufficiently pure to be polymerized to high molecular weight 6-nylon having good color and low gel content.

BACKGROUND OF THE INVENTION

The polymerization of 6-aminocapronitrile to form nylon polymer is disclosed in Greenewalt U.S. Pat. No. 2,245,129, and Curatolo et al. U.S. Pat. No. 4,568,736.

When 6-aminocapronitrile is produced by partial hydrogenation of adiponitrile, hexamethylenediamine and tetrahydroazepine, i.e. the latter compound represented by the formula:

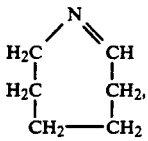

also coproduced. The hexamethylenediamine is easily removed from the mixture by simple distillation, but the tetrahydroazepine (hereinafter sometimes referred to as THA) is not easily separated. The presence of THA in the 6-aminocapronitrile (hereinafter sometimes referred to as 6-ACN) that is to be polymerized limits the molecular weight of the polymer and causes color and branching in the polymer. It is, therefore important that THA be removed from the 6-ACN before polymerization.

It is an object of the present invention to provide a simple and efficient method of obtaining 6-ACN that is free from THA.

The use of hydrides to prevent color formation in ethanol amines is disclosed in Moore U.S. Pat. No. 3,159,276, and the use of hydrides to reduce the color of ethanol amines is disclosed in Glew et al. U.S. Pat. No. 3,207,790. The use of sodium borohydride to reduce carbon/nitrogen double bonds in hetrocyclic compounds is also known and summarized in "Sodium Borohydride Digest" (1989) pages 24–26, Morton International, Specialty Chemicals Group.

SUMMARY OF THE INVENTION

The present invention is a process for the separation of 6-aminocapronitrile from a mixture also containing tetrahydroazepine which comprises treating the mixture with an effective amount of a hydride at a temperature between 20 and 70 degrees C. to convert tetrahydroazepine to hexamethyleneimine and N-(5-cyanopentyl)-1,6-hexamethylenediamine and then distilling the 6-aminocapronitrile at a pot temperature of less than about 200 degrees C.

Suitable hydrides include sodium borohydride, sodium cyanoborohydride, lithium borohydride, sodium borohydride anilide, lithium tri-tertbutoxy aluminum hydride, and sodium dimethoxyethoxy aluminum hydride.

The amount of hydride employed should normally be at least stoichiometrically equivalent to the amount of tetrahydroazepine, i.e. one mole of sodium borohydride per four moles of tetrahydroazepine, but a large excess of the hydride is entirely satisfactory, and some excess, 4 or 5 times the stoichiometric amount, is preferred.

It is preferable to also add water to the reaction mixture to increase the reaction rate. The amount of water required to produce the desired reaction rate will vary depending upon the concentration of the tetrahydroazepine in the mixture, but usually a water concentration of between about 2% and 6% by weight of the mixture is satisfactory.

The reaction temperature is important, in that at temperatures below about 20° C., the reaction is very slow, and at temperatures above about 70° C. the hydride causes the 6-aminocapronitrile to form additional by-products.

Reaction times of 30 hours or more are sometimes necessary to reduce the concentration of the THA to a satisfactory level.

After the THA concentration has decreased to the desired level, the 6-ACN is distilled from the reaction mixture. It is important that this distillation take place at a pot temperature of less than about 200° C., preferably less than 165° C. If the pot temperature is allowed to increase beyond 200° C., any excess hydride will cause some 6-ACN to react and form additional THA. Suitable industrial equipment for carrying out this distillation on a large scale is a wiped-film evaporator. The pressure of the distillation must be less than atmospheric. Pressures as high as 100 mm of mercury are operable, but it is preferable to operate at pressures of less than 80 mm of mercury. Good results are obtained at pressures in the range of 10 to 60 mm of mercury, but pressures as low as 0.25 mm of mercury are satisfactory although not attractive for large scale operation.

EXAMPLES

EXAMPLE 1

0.75 liter of 6-ACN containing 0.19% of THA (gas-chromatographic analysis) was treated with 2 grams (0.26%) of sodium borohydride at 70 degrees C. for 25 hrs. AT this time the THA analyzed as 0.076%. The 6-ACN was then distilled at a pressure of 0.4 mm Hg, pot temp of 80 deg C., head temp 63 deg C. The THA analysis of the distillate averaged about 0.02%.

EXAMPLE 2

40 ml of 6-ACN containing 0.44% of THA was treated with 0.5 g of sodium borohydride (1.25%) at 50 deg C. for 5 hrs. The THA level dropped to 0.36%. The solution was cooled to 25 deg C., and one ml of water was added. After 2 hrs, the THA level was 0.28%.

EXAMPLE 3

8.8 g of 6-ACN containing 0.44% THA was treated with 0.43 g water (4.9%) and 0.04 g of sodium borohydride (0.45%) at 25 deg C. After 3 hrs the THA measured 0.28%. Temperature was raised to 55 deg C. After 2.5 hrs at 55 deg, the THA measured 0.07%. After a total of 17.5 hrs at 55 deg, the THA measured 0.02%. A control at 55 deg C. not containing sodium borohydride contained 0.5% THA after 29.5 hrs.

EXAMPLE 4

100 g of 6-ACN containing 0.34% THA was heated at 50 deg C. for 21.5 hrs with 0.2 g sodium borohydride (0.2%) and 2 ml (2%) of water. The THA then measured 0.054%. Distillation was carried out at 100 mm, with a pot temperature of 175 deg, and a head temperature of 165 deg. A 15 g foreshot and a 75 g heartcut were taken. The foreshot contained 0.05% THA, and the heartcut 0.016% THA.

EXAMPLE 5

15,000 lbs of 6-ACN containing about 0.3% THA were mixed with a solution of 60.6 lbs of sodium borohydride in 600 lbs of water at 60 degrees C. for 30 hrs. The 6-ACN was distilled away from the sodium borohydride in a wiped-film evaporator at 10 mm Hg at about 105 degrees C. The overhead was refined through a standard packed column at about 160 degrees C. The resulting 6-ACN contained less than 0.01% THA.

I claim:

1. A process for the separation of 6-aminocapronitrile from a mixture also containing tetrahydroazepine which comprises treating the mixture with an effective amount of a hydride at a temperature between 20 and 70 degrees C. to convert tetrahydroazepine to hexamethyleneimine and N-(5-cyanopentyl)-1,6-hexamethylenediamine, and then distilling the 6-aminocapronitrile at a pot temperature of less than about 200° C.

2. The process of claim 1 in which the hydride is selected from the class consisting of sodium borohydride, sodium cyanoborohydride, lithium borohydride, sodium borohydride aniline, lithium tri-tertbutoxy aluminum hydride, and sodium di-methoxyethoxy aluminum hydride.

3. The process of claim 2 in which water is present in the mixture in an amount of up to about 6% by weight of the mixture.

4. The process of claim 1 in which the amount of hydride is at least stoichiometrically equivalent to the amount of tetrahydroazepine, and the pot temperature during distillation is less than 165° C.

* * * * *